United States Patent [19]

deWitt et al.

[11] 4,240,984

[45] Dec. 23, 1980

[54] PROCESS FOR PRODUCING AROMATIC ALDEHYDES

[75] Inventors: Paolo deWitt, Turin; Maria O. Tinti, Rome, both of Italy

[73] Assignee: Sigma-Tau Industrie Farmaceutiche Riunite S.p.A., Italy

[21] Appl. No.: 4,448

[22] Filed: Jan. 18, 1979

[30] Foreign Application Priority Data

Jan. 27, 1978 [IT] Italy ................................ 47813 A/78

[51] Int. Cl.$^3$ ............................................. C07C 45/41
[52] U.S. Cl. ................................. 568/435; 260/363
[58] Field of Search ................. 260/600 R, 599, 363; 568/814

[56] References Cited

U.S. PATENT DOCUMENTS

| | | | |
|---|---|---|---|
| 2,883,426 | 4/1959 | Brackman | 260/599 X |
| 3,322,833 | 5/1967 | McNelis | 260/599 |
| 3,855,306 | 12/1974 | Wehrli | 260/600 |
| 3,978,140 | 8/1976 | Lane et al. | 568/814 X |

FOREIGN PATENT DOCUMENTS 1123664  6/1956  France ...................................... 568/814

OTHER PUBLICATIONS

Tarbell et al., Jour. Org. Chem., vol. 23 (1958) 1149–1152.
Tarbell, Accounts of Chemical Research 2(10) 1969 290, 297–300.
Tarbell et al., Chemical Abstracts, vol. 50 (1956) 14727f.

*Primary Examiner*—Bernard Helfin
*Attorney, Agent, or Firm*—McGlew and Tuttle

[57] ABSTRACT

A process for preparing aromatic aldehydes starting from the corresponding aromatic acid, comprising two steps, the first one consisting of the reaction of said acid with ethyl or isobutyl chlorocarbonate to obtain the corresponding anhydride, and the second one to hydrogenate the thus-obtained anhydride to yield to aldehyde.

10 Claims, No Drawings

PROCESS FOR PRODUCING AROMATIC ALDEHYDES

The present invention relates to a general process for preparing aromatic aldehydes. More particularly, it relates to the preparation of benzaldehyde and derivatives thereof, such as, for instance, 3,4,5-trimethoxybenzaldehyde.

The industrial utility of benzaldehyde in the manufacture of colouring and aromatizing substances and as an intermediate in the production of cinnamic and mandelic acids is well-known, while 3,4,5-trimethoxybenzaldehyde is a previous intermediate in the synthesis of some important chemotherapeutic substances, especially of 2,4-diamino-5-(3,4,5-trimethoxy)benzylpyrimidine, known as Trimethoprin.

In view of the importance for the pharmaceutical industry of the synthesis of 3,4,5-trimethoxybenzaldehyde, and of the well-known difficulties and disadvantages (which will be illustrated in detail hereinafter) of the traditional processes of synthesis of said intermediate, the process for producing aromatic aldehydes of the present invention will be described particularly referring to the synthesis of said intermediate of benzaldehyde. It is to be understood however, as it is illustrated in the examples and is evident for anyone skilled in the art, that the present process has a general character and it can be applied, choosing an opportune starting material, to the preparation of other aromatic aldehydes.

It is well-known that there are numerous the processes for the preparation of 3,4,5-trimethoxy-benzaldehyde, but actually only two of these processes have a real industrial application, although both methods carry considerable inconveniences concerning the yields as well as the costs of the various compounds which are used in the course of the synthesis.

The first industrial synthetic method of making 3,4,5-trimethoxybenzaldehyde is based on the catalytic reduction of the chloride of 3,4,5-trimethoxy-benzoic acid, following the method of Rosemund, in aromatic solvent, containing a partial deactivating agent for the catalyst. The yields of this process are fluctuating (50–80%) and the quality of the obtained 3,4,5-trimethoxy-benzaldehyde is poor, since considerable amounts of secondary reduction products (like 3,4,5-trimethoxybenzyl alcohol and also 3,4,5-trimethoxy-toluene) are contained in the reaction mixture. Moreover this process requires the somewhat inconvenient and costly preparation of 3,4,5-trimethoxy-benzoic acid chloride.

The second industrial process concerns the preparation of 3,4,5-trimethoxy-benzaldehyde starting from vanilline, via 5-bromovanilline and a successive treatement with KOH and methanol is order to obtaine the required product. With this process, described in the U.S.A. Pat. No. 3,855,306, the yield of the second step is not industrially acceptable from the economical point of view. Also using this method, we fail, alter all, to obtain the product in good yields and at low costs.

The process of the present invention involves the preparation of 3,4,5-trimethoxy-benzaldehyde by reacting, at a first step, 3,4,5-trimethoxy-benzoic acid and ethyl or isobutyl chlorocarbonate, according to the method of mixed anhydrides and, at a second step, and by the catalytic reduction which leads directly from 3,4,5-trimethoxy-benzoyl-ethyl carbonate to the 3,4,5-trimethoxy-benzaldehyde. The compound formed during this first step may be directly utilized for the following step without any need of an isolation process. In fact the yields are practically quantitative, varying in the range of 93–95% and the operation leads to the formation of only a single substance: the 3,4,5-trimethoxybenzoyl-ethyl carbonate. This first reaction takes place in really mild conditions. (Atmospheric pressure, temperature 0°–15° C.).

In fact, operating without any special temperature and pressure conditions, the required product is obtained with such high yields and purity characteristics, that the cost of this raw material, produced in industrial scale, is remarkably more convenient than the cost of this substance produced by the hitherto known processes.

The preparation of 3,4,5-trimethoxy-benzoyl-ethyl carbonate is carried out either in tetrahydrofuran, or in benzene, or in any other inert solvent.

If the operation is carried out in a solvent which is proof against catalytic hydrogenation (as in the case of tetrahydrofuran) we are able to avoid the isolation of the formed mixed anhydride and therefore we can proceed directly to the hydrogenation.

3,4,5-trimethoxy-benzoic acid and ethyl chloroformate (these products can easily be found at low price on the market) are mixed together in the presence of an anhydrous base, for instance, trimethylamine at a temperature of 0°–15° C. The mass is kept stirred during a few hours and the trimethylamine chlorhydrate or any other base used is then eliminated by filtration. If the operation were carried out in a solvent inert against catalytic hydrogenation, we might directly proceed to the successive step.

It was found that the catalyst for the hydrogenation of the mixed anhydride to aldehyde is palladium 10% deposited on barium sulfate for instance (10% Pd/BaSO$_4$ ENGELHARD) preferably at the ratio of 50% in respect to the amount of 3,4,5-trimethoxy-benzoyl-ethyl carbonate used. In order to have high yields of 3,4,5-trimethoxy-benzaldehyde, it is necessary to partially poison the catalyst with a very dilute solution of sulfur and quinoline.

The operation is carried out at ordinary pressure and at room temperature. The reduction time is about 6–8 hours. All these conditions must be scrupulously observed in order to avoid the formation of secundary products.

By keeping the described conditions, the obtained yields are 90% of the theoretical amount, calculated in respect to the starting acid. The identity and the degree of purity of the requested product were checked by TLC, gas chromatography, IR, NMR and HPLC. Also the nature of the secundary products, which are possibly formed during the catalytic hydrogenation, were ascertained by means of HPLC and NMR.

The catalyst may be recycled for a certain number of steps and the recovery is always quantitative.

The reduction process may be continuous or discontinuous, according to the available type of plant.

The use of an industrial continuous process is preferable: that means that a continuous flow of 3,4,5-trimethoxy-benzoylethyl carbonate solution is passed through a column containing the catalyst, whereas, by the counter-current way, a calibrated flow of hydrogen is admitted. By that way, excellent yields are obtained, since the catalyst is always present in massive amounts in respect to the product subjected to the reduction; it is not necessary to proceed to filtrations of the catalyst and therefore a continuous process is effected without any product's manipulation. More generally, according to the present invention the process for preparing aromatic aldehydes comprises the following steps, starting from the corresponding aromatic acid:

(a) To react said aromatic acid at 0° to 15° C. and at atmospheric pressure, according to the mixed anhydrides method with ethyl or isobutyl chlorocarbonate, in the presence of an anhydrous base and of an anhydrous solvent, inert with respect to the reagents obtaining the corresponding anhydride; and (b) to hydrogenate the anhydride of step (a) directly to aldehyde for 6 to 8 hours, at atmospheric pressure and room temperature, in the presence of a hydrogenation catalyst comprising palladium on barium 10%, which preferably was previously poisoned, partially, with a solution of sulphur and quinoline. Preferably, the solution of sulphur and quinoline is between $2.5-6 \times 10^{-4}\%$ in sulphur and between 2 to $5 \times 10^{-4}\%$ in quinoline and even more preferably $4 \times 10^{-4}\%$ in sulphur and $3 \times 10^{-4}\%$ in quinoline. Moreover, the amount of the hydrogenation catalyst is preferably 40 to 60% in weight (even more preferably 50% in weight) with respect to the mixed anhydride of step (a).

The anhydrous solvent of step (a) is preferably proof against the subsequent hydrogenation: therefore, it is not necessary to isolate the mixed anhydride from the reaction step containing the same, before proceeding to hydrogenation thereof. To this end, tetrahydrofuran is a particularly preferred solvent while other solvents will be evident to one skilled in the art.

Non-limitative examples of aromatic acids that can be transformed into the corresponding aldehydes by the process of the present invention comprise: benzoic acid; phenylacetic acid; ortho, meta and para-toluic acid; ortho, meta and para chloro (or bromo) benzoic acid; trialkoxybenzoic acids, such as, for instance, 3,4,5-trimethoxybenzoic acid and the like. The corresponding aldehydes also include benzaldehydes substituted with, lower alkyl radicals, lower alkoxy groups, and halogens, particularly chlorine and bromine. The following non-limitative examples are given for a better elucidation of the described invention.

EXAMPLE I.

Step (a): preparation of 3,4,5-Trimethoxy-ethyl carbonate.

10.8 g (0.10 moles) of ethyl chloroformate are dissolved in ml 100 of tetrahydrofuran. This solution is then added under stirring and cooling at 5°-10° C., during 10-30 minutes to a solution of 21.2 g (0.10 moles) of 3,4,5-trimethoxy-benzoic acid and 12.12 g (0.12 moles) of triethylamine in 200 ml of tetrahydrofuran. At the end of the addition the reaction mixture is kept at the room temperature during 2 hours under continuous stirring.

The so-formed precipitate is filtered, throughly washed with tetrahydrofuran, and discarded.

On the joined reaction solution and washing liquids, we may directly proceed to the catalytic reduction for the preparation of the 3,4,5-trimethoxy-benzaldehyde.

The 3,4,5-trimethoxy-benzoyl-ethyl carbonate may be isolated by means of complete evaporation under a vacuum of the mother liquids at the temperature between 50° C. and 70° C. The residue is a white microcristalline solid (26.7 g; yield 94%) with following characteristics:

M.P. 92°-94° spectrum IR: $\lambda = 1810$ and $1710$ cm$^{-1}$ spectrum NMR: $(CD_3)_2$ SO $\delta$: 7.4 (s,2H, aromatics) 4.4; (q,2H,—$\underline{CH_2}$—CH$_3$); 3.9 (s, 6H,3.5—OCH$_3$); 3.8 (s, 3H, 4—OCH$_3$); 1.35 (t,3H,—CH$_2$—$\underline{CH_3}$)

Anal.: C=54.85% H=5.34%

The substance is remarkably stable and keeps well also at room temperature. It is not affected by moisture.

Step (b): Reduction to 3,4,5-trimethoxy-benzaldehyde.

To a solution of 28.4 g (10.1 moles) of 3,4,5-trimethoxy-benzoylethyl carbonate in ml 300, prepared as described in step (a), 14.2 g of Pd supported on BaSO$_4$ (10%) and 0.1 ml of a solution of sulfur and quinoline prepared following Rosemund and Zetzsche and diluted 1:3000 are added. The mixture is hydrogenated in a PARR apparatus in an hydrogen atmosphere at ordinary pressure and 25° C. under efficient shaking during 12 hours. The catalyst is removed by filtration and recovered, whereas the organic solution is washed with a 5% NaOH solution and finally evaporated in a vacuum. 17.64 g of 3,4,5-trimethoxybenzaldehyde are obtained, with the same characteristics generally described in the literature.

EXAMPLE II.

3,4,5-trimethoxy-benzaldehyde.

A column thermostated at 25° C., 20 cm long with a diameter of 2 cm is prepared in the following way: at the bottom it is filled with 5 cm of an inert porous support and afterwards with cm 12 of Pd/BaSO$_4$ (10%) (about 50 g). Finally further cm 5 of the same inert, porous support used for filling the base, are stratified on the top.

The catalyst is loaded in a moisted state, after a 2 hours treatment with tetrahydrofuran containing 0.2 ml of a solution of sulfur and quinoline prepared as in example I.

A solution containing g 900 of 3,4,5-trimethoxy-benzoyl-ethyl carbonate (prepared as in Example I, step (a)) in 9000 ml of tetrahydrofuran is percolated from the top of the column through the catalyst, with a flow of 20 ml per minute, whereas a light stream of hydrogen is admitted in conter-current.

After about 8 hours the whole solution containing 3,4,5-trimethoxy-benzoyl-ethyl-carbonate is percolated through the column and is collected in a suitable container, where it is washed with a 5% NaOH solution and finally dried under a vacuum. In this way 530 g of 3,4,5-trimethoxy-benzaldehyde (87%) with all the characteristics described in example I step (b), are collected. The catalyst contained in the column remains in the condition to be able to carry out further reductions of the product with the same efficiency demonstrated in the above described reduction. This system may be applied for a continuous reduction of a big amount of 3,4,5-trimethoxy-benzoyl-ethyl carbonate to 3,4,5-trimethoxy-benzaldehyde.

EXAMPLE III

Step (a): Preparation of benzoyl-ethyl-carbonate 10.8 g (0.10 moles) of ethylchloroformate dissolved in 100 ml of tetrahydrofuran are added to a tetrahydrofuran solution (200 ml) containing 12.2 g (0.10 moles) of benzoic acid and 12.12 g (0.12 moles) of triethylamine. We proceed as in Example I, step (a). There are obtained 17.8 g (yield 92%) of the product mentioned in the title, having the following characteristics:

Elementar analysis: C=61.85%; H=5.19%

Spectrum NMR: $(CD_3)_2SO$ $\delta = 8.2$-$7.4$ (m, 5 H, aromatics); 4.4 (q,2H, —$CH_2$—$CH_3$); 1.3 (t, 3H,— $CH_2$—$CH_3$).

step (b): Reduction to benzaldehyde

To a solution containing 19.4 g (0.10 moles) of benzoyl-ethyl carbonate in 300 ml of tetrahydrofuran there are added 9.7 g of Pd on $BaSO_4$ 10% and 0.1 cc of a solution of sulfur and quinoline 1:3000.

Proceeding as in Example I, step (b) 9.7 g of benzaldehyde (yield 92%) are obtained.

EXAMPLE IV

Step (a): Preparation of p-toluyl-ethyl-carbonate 10.8 g (0.10 moles) of ethylchloroformiate dissolved in 100 ml of tetrahydrofuran are added to a solution of tetrahydrofuran (200 ml) containing 13.6 g (0.10 moles) of p-toluic acid and 12.12 g (0.12 moles) of triethylamine. We proceed as in Example I, step (a). There are obtained 18.7 g (yield 90%) of a product having the following characteristics:

Elementar analysis: C=63.45%; H=5.80%

Spectrum NMR: $(CD_3)_2SO$ $\delta = 8.0$ (d,2H aromatics); 7.2 (d,2H aromatics); 2.4 (s,1H $CH_3$—); 4.4 (q,2H-$CH_2$—$CH_3$); 1.3 (t,3H-$CH_2$—$Ch_3$).

step (b): Reduction to p-methyl-benzaldehyde

To a solution containing 20.8 g (0.10 moles) of p-toluylethyl-carbonate in 300 ml of tetrahydrofuran there are added 10.4 g of Pd on $BaSO_4$ 10% and 0.1 cc of a solution of sulfur and quinoline 1:3000. Proceeding as in Example I, step (6), 10.5 g of p-methylbenzaldehyde (yield 88%) are obtained.

EXAMPLE V

Step (a) - Preparation of p-chloro-benzoyl-ethyl-carbonate 10.8 g (0.10 moles) of ethylchloroformiate dissolved in 100 ml of tetrahydrofuran are added to a solution of tetrahydrofuran (200 ml) containing 15.6 g (0.10 moles) of p-chlorobenzoic acid and 12.12 g (0.12 moles) of triethylamine. Proceeding as in Example I, step (a), there are obtained 21 g (yield 92%) of a product having the following characteristics:

Elementary analysis: C=52.53%; H=3.96%

Spectrum NMR: $(CD_3)_2SO$ $\delta = 7.9$ (d,2H, aromatics); 7.4 (d,2H, aromatics); 4.4 (q,2H,-$\underline{CH_2}$—$CH_3$); 1.3 (t,3H,-$CH_2$—$CH_3$).

step (b): Reduction to p-chloro benzaldehyde

To a solution containing 22.8 g (0.10 moles) of p-chloro-benzoyl-ethyl-carbonate in 300 ml of tetrahydrofuran there are added 12.4 g of Pd on $BaSO_4$ 10% and 0.1 of a solution of sulfur and quinoline 1:3000. Proceeding as in Example I, step (b) 12.5 g of p-chlorobenzaldehyde (yield 89%) are obtained.

What is claimed is:

1. Process for preparing benzaldehyde or benzaldehyde substituted with; lower alkyl radicals, lower alkoxy groups, chlorine or bromine; starting from the corresponding aromatic acid, which comprises the following steps:
   (a) reacting said aromatic acid at 0°-15° C. and at atmospheric pressure with ethyl or isobutyl chlorocarbonate, in the presence of an anhydrous base and an anhydrous solvent, inert in respect to the reagents, and obtaining the corresponding anhydride;
   (b) hydrogenating directly to aldehyde the anhydride of step (a) for 6-8 hours at atmospheric pressure and at room temperature, in the presence of a hydrogenation catalyst comprising 10% by weight palladium on barium sulphate, said hydrogenation catalyst being partially poisoned before use thereof by a solution of sulphur and quinoline in an inert solvent containing between 2.5 and $6 \times 10^{-4}$ by weight in sulphur and between 2 and $5 \times 10^{-4}$% by weight in quinoline.

2. Process according to claim 1, wherein said solution of sulphur and quinoline is $4 \times 10^{-4}$% in sulfur and $3 \times 10^{-4}$% in quinoline.

3. Process according to claim 2, wherein the amount of catalyst is from about 40 to 60% by weight in respect to the anhydride of step (a).

4. Process according to claim 1, wherein said anhydrous solvent is not affected by the catalytic hydrogenation of step (b).

5. Process according to claim 4, wherein said anhydrous solvent is tetrahydrofuran.

6. Process for preparing phenylacetaldehyde, ortho-meta-, or para-toluic aldehyde, starting from the corresponding aromatic acid, which comprises the following steps:
   (a) reacting said aromatic acid at 0°-15° C. and at atmospheric pressure with ethyl or isobutyl chlorocarbonate, in the presence of an anhydrous base and an anhydrous solvent, inert in respect to the reagents, and obtaining the corresponding anhydride;
   (b) hydrogenating directly to aldehyde the anhydride of step (a) for 6-8 hours at atmospheric pressure and at room temperature, in the presence of a hydrogenation catalyst comprising 10% by weight palladium on barium sulphate, said hydrogenation catalyst being partially poisoned before use thereof by a solution of sulphur and quinoline in an inert solvent containing between 2.5 and $6 \times 10^{-4}$ by weight in sulphur and between 2 and $5 \times 10^{-4}$ by weight in quinoline.

7. Process according to claim 6, wherein said solution of sulphur and quinoline is $4 \times 10^{-4}$ in sulphur and $3 \times 10^{-4}$ in quinoline.

8. Process according to claim 7, wherein the amount of catalyst is from about 40 to 60% by weight in respect to the anhydride of step (a).

9. Process according to claim 6, wherein said anhydrous solvent is not affected by the catalytic hydrogenation of step (b).

10. Process according to claim 9, wherein said anhydrous solvent is tetrahydrofuran.

* * * * *